(12) United States Patent
Guger et al.

(10) Patent No.: US 10,758,148 B2
(45) Date of Patent: Sep. 1, 2020

(54) ELECTRODE CAP

(71) Applicants: Christoph Guger, Piberbach (AT); Guenter Edlinger, Graz (AT)

(72) Inventors: Christoph Guger, Piberbach (AT); Guenter Edlinger, Graz (AT)

(*) Notice: Subject to any disclaimer, the term of this patent is extended or adjusted under 35 U.S.C. 154(b) by 100 days.

(21) Appl. No.: 16/083,579

(22) PCT Filed: Mar. 6, 2017

(86) PCT No.: PCT/AT2017/060056
§ 371 (c)(1),
(2) Date: Sep. 10, 2018

(87) PCT Pub. No.: WO2017/152206
PCT Pub. Date: Sep. 14, 2017

(65) Prior Publication Data
US 2019/0082994 A1    Mar. 21, 2019

(30) Foreign Application Priority Data

Mar. 9, 2016 (AT) .............................. A 50198/2016

(51) Int. Cl.
*A61B 5/0408* (2006.01)
*A61B 5/0478* (2006.01)
(Continued)

(52) U.S. Cl.
CPC .......... *A61B 5/0478* (2013.01); *A61B 5/0428* (2013.01); *A61B 5/04085* (2013.01);
(Continued)

(58) Field of Classification Search
CPC ... A61B 5/0478; A61B 5/0488; A61B 5/6803; A61B 5/6814
(Continued)

(56) References Cited

U.S. PATENT DOCUMENTS

| | | | |
|---|---|---|---|
| 5,038,782 A | 8/1991 | Gevins et al. | |
| 7,715,894 B2* | 5/2010 | Dunseath | ............. A61B 5/0478 600/372 |

(Continued)

FOREIGN PATENT DOCUMENTS

| | | |
|---|---|---|
| EP | 2886049 A1 | 6/2015 |
| FR | 2627975 A1 | 9/1989 |

(Continued)

OTHER PUBLICATIONS

Chowdhury et al., "Reference layer artefact subtraction (RLAS): A novel method of minimizing EEG artefacts during simultaneous fMRI", NeuroImage, 84, (2014), pp. 307-319.

(Continued)

*Primary Examiner* — Lee S Cohen
(74) *Attorney, Agent, or Firm* — Laurence A. Greenberg; Werner H. Stemer; Ralph E. Locher

(57) ABSTRACT

An electrode cap contains at least one electrode array and is to be applied to a subject's head. The electrode array contains an insulating layer, two electrodes disposed opposite one another on the insulating layer, namely a first measurement electrode facing toward the subject's head and a reference electrode facing away from the subject's head. A conductive body abuts the reference electrode and is in electrical contact therewith, and is arranged on the side of the reference electrode that faces away from the subject's head. The individual conductive bodies of all the electrode arrays are electrically connected to each other.

16 Claims, 2 Drawing Sheets

(51) Int. Cl.
  *A61B 5/00* (2006.01)
  *A61B 5/0428* (2006.01)
  *A61B 5/0488* (2006.01)
  *A61B 5/05* (2006.01)

(52) U.S. Cl.
  CPC .............. *A61B 5/0488* (2013.01); *A61B 5/05* (2013.01); *A61B 5/6803* (2013.01); *A61B 5/6814* (2013.01); *A61B 2562/0209* (2013.01)

(58) Field of Classification Search
  USPC ........................................................ 600/383
  See application file for complete search history.

(56) References Cited

U.S. PATENT DOCUMENTS

| | | | |
|---|---|---|---|
| 9,072,448 B2 | 7/2015 | Fadem | |
| 2009/0054758 A1 | 2/2009 | Dunseath | |
| 2009/0099473 A1 | 4/2009 | Dunseath et al. | |
| 2013/0172721 A1 | 7/2013 | McPeck et al. | |
| 2015/0011857 A1* | 1/2015 | Henson | A61B 5/6831 600/383 |
| 2016/0331328 A1* | 11/2016 | Looney | A61B 5/0492 |

FOREIGN PATENT DOCUMENTS

| | | |
|---|---|---|
| GB | 2522195 A | 7/2015 |
| WO | 2011038103 A1 | 3/2011 |

OTHER PUBLICATIONS

Luo Et At., "Ballistocardiogram Artifact Removal with a Reference Layer and Standard EEG Cap", J. Neurosci Methods, Aug. 15, 2014 (Aug. 15, 2014), 233: 137-149, DOI: 10.1016/jneumeth.2014.06.021.

Xia et al., "Removing ballistocardiogram (BCG) artifact from full-scalp EEG acquired inside the MR scanner with Orthogonal Matching Pursuit (OMP)", Frontiers in Neuroscience, vol. 8, Jul. 29, 2014 (Jul. 29, 2014), Article 218.

Heimatlexikon—Our Austria, "Geschichte der Kopfbedeckung" [History of Headgear], a project of SERVUS TV in coperation with the Austria-Forum, https://austria-forum.org/af/Heimatlexikon/Geschichte_der_Kopfbedeckung, pp. 1-3—English version.

* cited by examiner

ELECTRODE CAP

BACKGROUND OF THE INVENTION

Field of the Invention

The invention relates to an electrode cap comprising at least one electrode array to be applied to the subject's head.

The invention further relates to an EEG measuring arrangement.

A large number of different electrode caps to be applied to a subject's head are known from the prior art. In general, such electrode caps have the drawback that measurement signals at individual electrodes are subject to different disturbances.

SUMMARY OF THE INVENTION

The objective of this invention is to provide an electrode cap that is largely unaffected by interference emanating from electromagnetic fields or structures outside the electrode cap. The present invention solves this problem with an electrode cap of the above-mentioned type, having the features of claim 1.

It is contemplated that each of the electrode arrays comprises:
an insulating layer,
two electrodes opposite one another on the insulating layer, namely a first measurement electrode facing toward the subject's head and a reference electrode facing away from the subject's head, and
a conductive body that abuts the reference electrode and is in electrical contact therewith, arranged on the side of the reference electrode facing away from the subject's head, and
wherein the individual conductive bodies of all electrode arrays are electrically connected to each other.

It is particularly advantageous that electromagnetic influences from outside the electrode cap via the continuous conductive body affect the measurement signals of all electrodes equally, so that signals that are completely independent of the external electromagnetic influences or interference may be obtained by simple compensation.

Particularly preferably, for connecting a measuring arrangement to a common system ground, it may be contemplated that a reference electrode array is provided, for applying to the subject's head, that has at least one electrode facing toward the subject's head and is electrically connected to the individual conductive bodies of the electrode arrays.

In a particularly structurally simple embodiment of the invention, it is contemplated that the conductive body of the reference electrode array is electrically conductively connected to the conductive bodies of all the electrode arrays.

A simple possibility for creating a continuous conductive body contemplates that the conductive body of the or each electrode array, optionally of the reference electrode array, is formed by a fluid that is in electrical contact with the reference electrode and/or the second electrode, in particular a saline solution, and/or that the conductive body has a specific conductivity between 2 mS/cm and 40 mS/cm.

In this case, for the modular design of individual electrode arrays it may be contemplated that the individual electrode arrays and optionally the reference electrode array respectively have a container bounded by the reference electrode and/or the second electrode, in which the fluid is contained, and that the individual containers are connected and thus form vessels that communicate with one another, in particular via hose connections.

To provide a particularly simple modular adaptation of the electrode cap to different head shapes, the electrode cap may be formed as a tubular network of electrode arrays connected to one another via hose connections, wherein the individual containers of the electrode arrays have connectors for connecting, in particular reversibly, with the hose connections.

A particularly advantageous contacting of the subject's head to the electrode cap contemplates that at least one or each of the electrode arrays, and optionally the reference electrode array, has a recess for receiving a conductive gel, the recess being bounded by the measurement electrode or the first electrode and being open toward the subject's head.

An advantageous measuring arrangement comprises an electrode cap according to the invention and a measuring device for determining the voltages applied to the electrodes. Particularly advantageously, for further processing of the signals, a processing unit may be furnished that relates those electrical signals that are respectively applied to the measurement electrode and the reference electrode of the same electrode array to each other, and in particular subtracts the two signals from each other, thus creating a cleaned signal for the electrode array.

To provide a reference potential, particularly simply, the at least one electrode or the two electrodes of the reference electrode array may be connected to a reference potential of the measuring device.

A preferred embodiment of the invention is illustrated in greater detail with reference to the following drawings.

DESCRIPTION OF THE INVENTION

Figure 1:
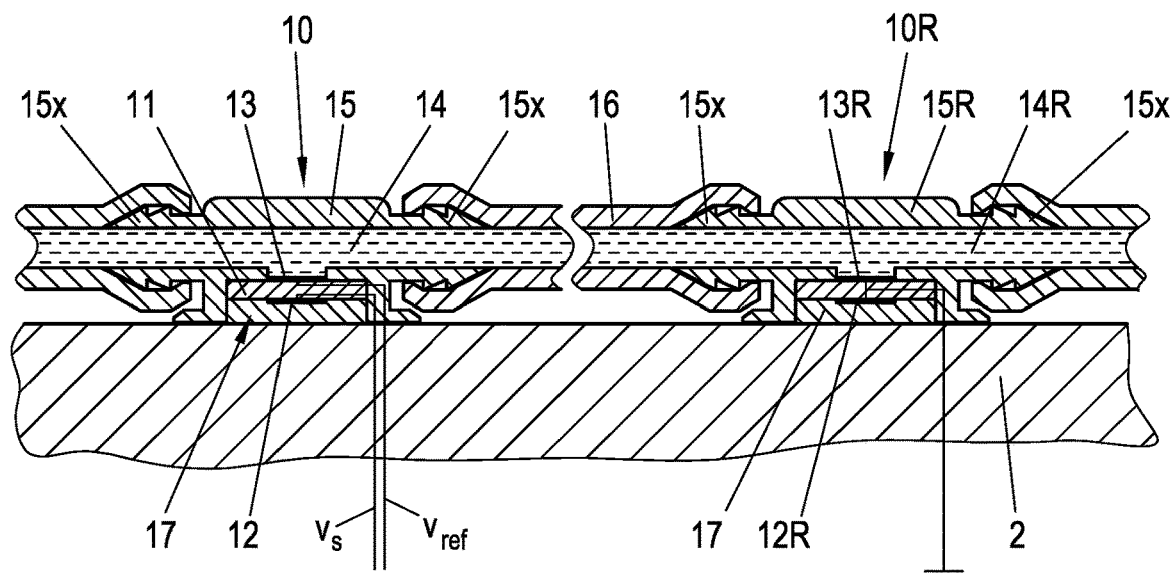
FIG. 1 shows schematically the structure of two electrode arrays having a common conductive body.

In FIG. 1, the subject's head 2 is shown, to which are connected an electrode array 10 and a reference electrode array 10R. The first electrode array 10 comprises an insulating layer 11 and two electrodes 12, 13 opposite one another on the insulating layer 11. The first of the two opposing electrodes 12 is located on the side facing toward the subject's head 2. The electrode array 10 has a recess 17 for receiving conductive gel, which is bounded by the first electrode 10 and is open toward the subject's head 2. Conductive gel may be inserted into this recess 17 so that the first electrode 12 is in electrical contact with the subject's head 2.

Furthermore, each of the electrode arrays 10 respectively has a reference electrode 13 arranged on the side of the insulating layer 11 opposite the measurement electrode 12. The reference electrode 13 is in electric contact with a conductive body 14 that abuts the reference electrode 13. The conductive body 14 is arranged on the side of the reference electrode 13 that faces away from the subject's head 2. The electrode cap 1 comprises a plurality of electrode arrays 10 each having a separate insulating layer 11 and respectively separate electrodes 12, 13 lying opposite one another. For all or part of the electrode arrays 10, a common conductive body 14 is respectively available. Alternatively it may also be contemplated that for each of the electrode arrays 10 there is respectively a separate conductive body 14 and all of the conductive bodies 14 of the individual electrode arrays 10 are electrically connected to each other.

In the embodiment of the invention shown in FIG. 1, a reference electrode array 10R for applying to the subject's head 2 is furnished, in addition to the electrode array 10. The reference electrode array 10R is substantially structured like the electrode array 10, and more particularly has an electrode 12R facing toward the subject's head 2. Overall, however, it is only necessary that a single electrode 12R be furnished on the side facing toward the subject's head 2, which is conductively connected in whatever way to the individual conductive bodies of the reference electrode array 10R. Such a reference electrode array 10R may be implemented particularly advantageously if it is designed in the same way as the individual electrode arrays 10, the reference electrode array 10R comprising:

an insulating layer 11, two electrodes 12R, 13R opposite one another on the insulating layer 11, namely a first electrode 12R facing toward the subject's head 2 and a second electrode 13R facing away from the subject's head 2, wherein the first and second electrode 13R are electrically connected together, a conductive body 14R abutting the second electrode 13R and in electrical contact therewith, which is arranged on the side of the second electrode 13R that faces away from the subject's head 2.

The conductive body 14R of the reference electrode array 10R is electrically connected to the conductive bodies 14 of the electrode arrays 10.

As also initially described with regard to the electrode arrays 10, there is preferably also a possibility for the reference electrode array 10R to be furnished with a recess 17, for receiving conductive gel, bounded by the first electrode 12R and open toward the subject's head 2.

Figure 2:
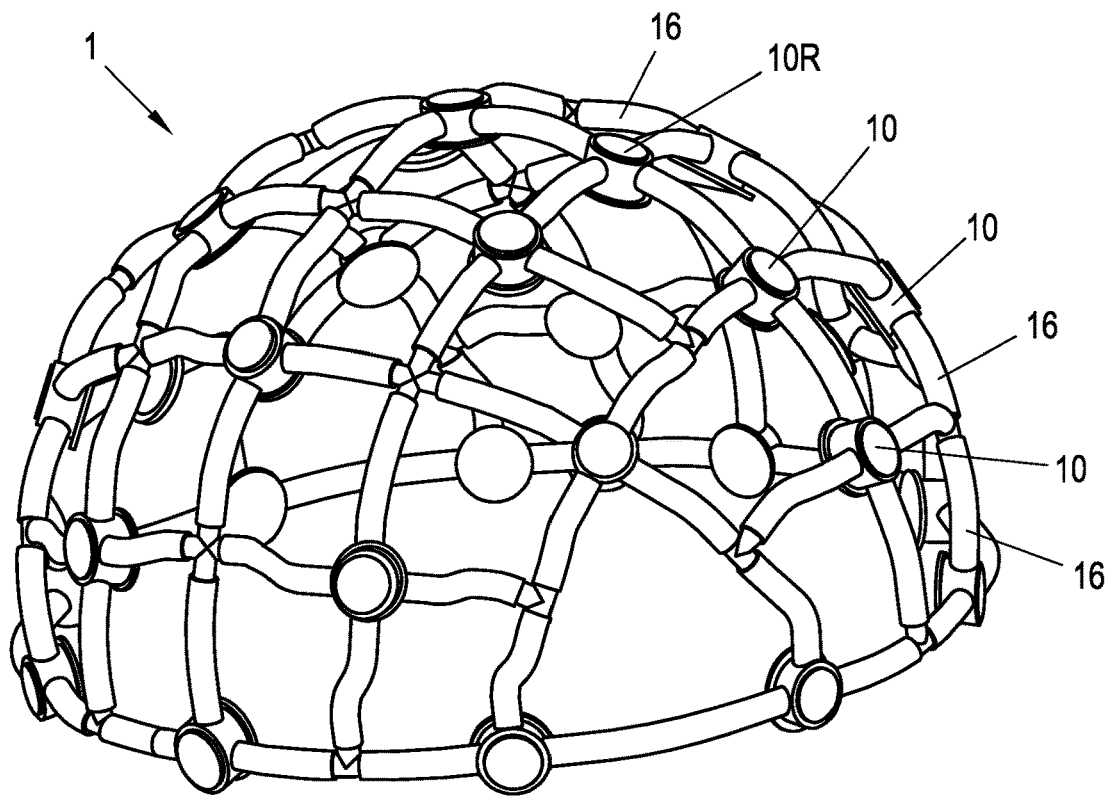
FIG. 2 shows the structure of an electrode cap in its entirety.

FIGS. 1 and 2 show a particularly preferred embodiment of the invention in greater detail, providing a common conductive body 14 formed by a fluid, in particular a saline solution, that is in contact with the individual reference electrodes 13 and optionally the second electrode 13R. The conductive body 14 in this preferred embodiment of the invention has a specific conductivity between 2 mS/cm and 40 mS/cm.

As shown in FIG. 1, each individual electrode array 10 and the reference electrode array 10R respectively have a container 15, 15R bounded by the reference electrode 13 and the second electrode 13R. The fluid that forms the conductive body 14 is contained in this container. The individual containers 15, 15R of the electrode array 10 or reference electrode array 10R are connected to one another via hose connections 16, and thus form a communicating vessel. As shown in FIG. 2, each of the electrode arrays 10 and reference electrode arrays 10R respectively has a number of connectors 15X for hose connections 16. The individual electrode arrays of the present exemplary embodiment each respectively have four hose connections 15X. The number of hose connections 15X may however vary, for example between two and ten. The electrode cap 1 is formed as a tubular network of electrode arrays 10, 10R connected together by hose connections 16. In this preferred embodiment of the invention, the hose connections 16 may be reversibly released from the connectors 15X. As shown in FIG. 2, there is the possibility that the individual hose connections 16R may open into T-junctions adjacent to the containers 15 of the electrode arrays 10. In addition, there is also the possibility that individual hose connections 16 may be connected to an external inflow hose and an external outflow hose, via which fluid may be pumped into the electrode cap 1 or the hose network, or via which fluid may be pumped out from the hose network or the electrode cap 1.

Figure 3:
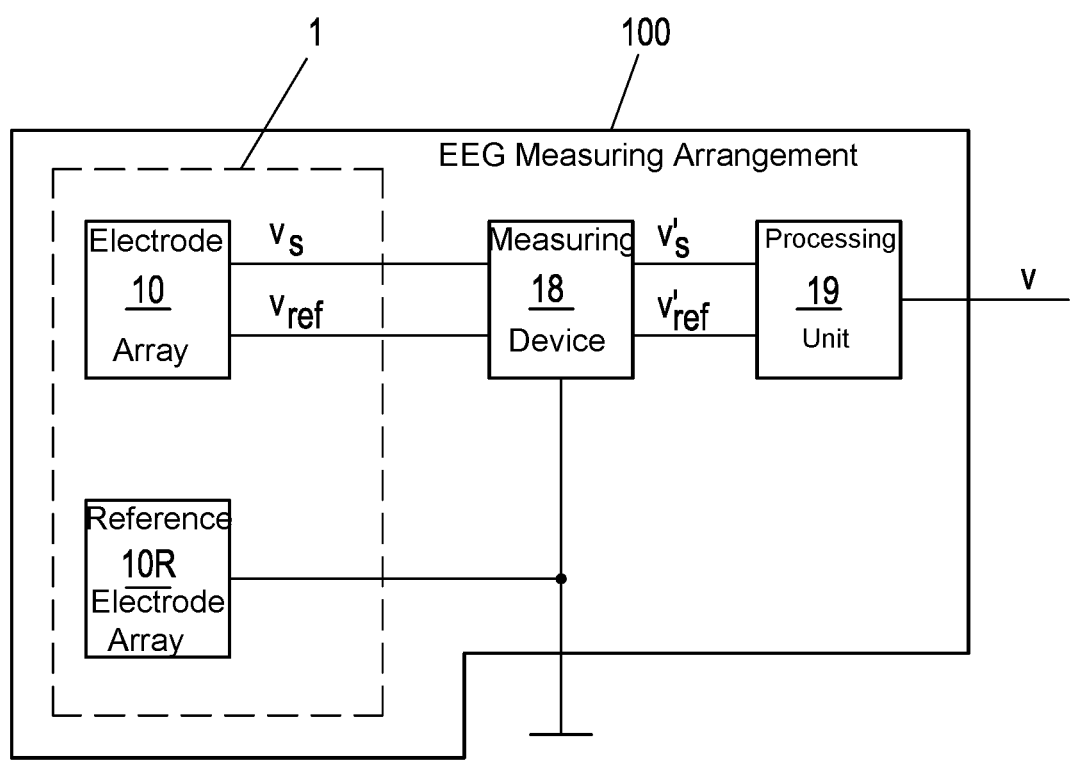
FIG. 3 shows an EEG measuring arrangement corresponding to an exemplary embodiment of the invention.

FIG. 3 shows an EEG measuring arrangement 100 corresponding to an exemplary embodiment of the invention. This EEG measuring arrangement 100 comprises an electrode cap 1 as shown in FIGS. 1 and 2 and a measuring device 18 for measuring electrical voltages or voltage signals. The individual electrodes 12, 13 of the electrode arrays 10 are electrically connected to the measuring device 18. The electrodes 12R of the reference electrode array 10R are also connected to the electrical measuring device 18. In this specific case, the two electrodes 12R, 13R of the reference electrode array 10R are connected to the reference potential of the measuring device 18. The measuring device 18 continuously determines the individual voltages applied to the electrodes 12, 13 and thus provides signals $V_S$, $V_{ref}$. The EEG measuring arrangement 100 comprises a processing unit 19, which is downstream of the electrical measuring arrangement. This processing unit 19 relates the individual electrical signals $V_S$, $V_{ref}$ received by the measuring device 18 and which are applied to the measurement electrode 12 and the reference electrode 13 of the same electrode array 10 respectively. In a preferred embodiment of the invention, the two signals are subtracted from one another and thus a cleaned signal V is formed, which is provided at the output.

The invention claimed is:

1. An electrode cap, comprising:
electrode arrays to be applied to a subject's head, each of said electrode arrays containing:
an insulating layer;
two electrodes disposed opposite one another on said insulating layer, said two electrodes include a first measurement electrode adapted to face toward the subject's head and a second electrode adapted to face away from the subject's head;
a conductive body abutting said second electrode and in electrical contact therewith, said conductive body disposed on a side of said second electrode that is adapted to face away from the subject's head;
said conductive body is electrically connected to said conductive body of other ones of said electrode arrays; and
said conductive body of at least one of said electrode arrays is formed by a fluid which is in electrical contact with said second electrode.

2. The electrode cap according to claim 1, further comprising a reference electrode array for applying to the subject's head, said reference electrode array having at least one reference electrode that is adapted to face toward the subject's head and is electrically connected to said conductive bodies of said electrode arrays.

3. The electrode cap according to claim 2, wherein said reference electrode array contains:
a reference insulating layer;
two reference electrodes disposed opposite one another on said reference insulating layer, and including a first reference electrode adapted to face toward the subject's head and a second reference electrode adapted to face away from the subject's head, said first and second reference electrodes are electrically connected; and a conductive reference body abutting said second reference electrode and in electrical contact with said second reference electrode, said conductive reference body is disposed on a side of said second reference electrode that is adapted to face away from the subject's head, said conductive reference body of said reference electrode array is electrically connected to said conductive bodies of said electrode arrays.

4. The electrode cap according to claim 3, wherein said conductive reference body is formed by said fluid and is in electrical contact with said second reference electrode.

5. The electrode cap according to claim 4, wherein at least one of said electrode arrays or said reference electrode array each respectively has a container bounded by said second electrode or said second reference electrode, in which said fluid is contained, and said container of each of said electrode arrays and/or said reference electrode array are connected and thus form vessels communicating with each other.

6. The electrode cap according to claim 5, further comprising hose connections and the electrode cap is formed as a tubular network of said electrode arrays connected to one another via said hose connections, wherein said containers of said electrode arrays have connectors for connecting with said hose connections.

7. The electrode cap according to claim 6, wherein said connectors connect reversibly with said hose connections.

8. The electrode cap according to claim 5, further comprising hose connections connecting said containers to each other.

9. The electrode cap according to claim 3, wherein at least one of said electrode arrays has a recess formed therein for receiving a conductive gel, said recess being bounded by said first measurement electrode and being open on a side adapted to face toward the subject's head.

10. The electrode cap according to claim 9, wherein said reference electrode array has a reference recess formed therein for receiving said conductive gel, said reference recess being bounded by said first reference electrode and being open on a side adapted to face toward the subject's head.

11. The electrode cap according to claim 1, said fluid is a saline solution.

12. The electrode cap according to claim 1, wherein said conductive body has a specific conductivity of between 2 mS/cm and 40 mS/cm.

13. An electroencephalogram measuring configuration, comprising:
  an electrode cap containing electrode arrays to be applied to a subject's head, each of said electrode arrays having an insulating layer, two electrodes disposed opposite one another on said insulating layer, said two electrodes having a first measurement electrode adapted to face toward the subject's head and a second electrode adapted to face away from the subject's head, and a conductive body abutting said second electrode and in electrical contact therewith, said conductive body disposed on a side of said second electrode that is adapted to face away from the subject's head, and said conductive body is electrically connected to said conductive body of other ones of said electrode arrays, wherein said conductive body of at least one of said electrode arrays is formed by a fluid which is in electrical contact with said second electrode;
  an electrical measuring device; and
  said electrodes of said electrode arrays are electrically connected to said electrical measuring device for measuring voltages and/or electrical signals applied to said electrodes.

14. The EEG measuring configuration according to claim 13, further comprising a processing unit that relates the electrical signals that are present respectively at said first measurement electrode and said second electrode of a same one of said electrode arrays to each other, and subtracts the two electrical signals from each other, and thus creates a cleaned signal for said same one electrode array, said processing unit is connected to said electrical measuring device.

15. The EEG measuring configuration according to claim 13, wherein said electrode cap contains a reference electrode array for applying to the subject's head, said reference electrode array having:
  a reference insulating layer;
  two reference electrodes disposed opposite one another on said reference insulating layer, and including a first reference electrode adapted to face towards the subject's head and a second reference electrode adapted to face away from the subject's head, said first and second reference electrodes are electrically connected; and
  a conductive reference body abutting said second reference electrode and in electrical contact therewith, said conductive reference body is disposed on a side of said second reference electrode that is adapted to face away from the subject's head, said conductive reference body of said reference electrode array is electrically connected to said conductive body of said electrode arrays.

16. The EEG measuring configuration according to claim 15, wherein said first reference electrode or said two reference electrodes of said reference electrode array are connected to a reference potential of said electrical measuring device.

* * * * *